(12) United States Patent
Estor et al.

(10) Patent No.: US 9,029,779 B2
(45) Date of Patent: May 12, 2015

(54) TIRE SURFACE ANOMALY DETECTION

(75) Inventors: Patrice R. Estor, Greer, SC (US); Julien Matthieu Flament, Clemont-Ferrand (FR); Verner Steve Nicholson, Pelzer, SC (US); Anton Felipe Thomas, Greer, SC (US); Gene Edward De Amicis, Mt. Pleasant, SC (US); Frank E. Gramling, Simpsonville, SC (US); David Andrew Judd, Mauldin, SC (US); Bradley D. Schober, Greer, SC (US)

(73) Assignees: Michelin Recherche et Technique S.A., Granges-Paccot (CH); Compagnie Generale des Etablissements Michelin, Clermont-Ferrand (FR)

( * ) Notice: Subject to any disclaimer, the term of this patent is extended or adjusted under 35 U.S.C. 154(b) by 107 days.

(21) Appl. No.: 13/704,436

(22) PCT Filed: Jun. 15, 2010

(86) PCT No.: PCT/US2010/038634
§ 371 (c)(1),
(2), (4) Date: Dec. 14, 2012

(87) PCT Pub. No.: WO2011/159280
PCT Pub. Date: Dec. 22, 2011

(65) Prior Publication Data
US 2013/0099123 A1    Apr. 25, 2013

(51) Int. Cl.
*G01J 5/02* (2006.01)
*G01N 21/95* (2006.01)
*G06T 7/00* (2006.01)

(52) U.S. Cl.
CPC .............. *G01N 21/95* (2013.01); *G06T 7/0004* (2013.01); *G06T 2207/10048* (2013.01)

(58) Field of Classification Search
USPC ....................................................... 250/341.6
See application file for complete search history.

(56) References Cited

U.S. PATENT DOCUMENTS 4,479,139 A * 10/1984 Parrish .......................... 257/226
4,785,354 A    11/1988 Nakamura et al.
(Continued)

FOREIGN PATENT DOCUMENTS

EP    0514162    11/1992
EP    0580024    1/1994
(Continued)

OTHER PUBLICATIONS

International Search Report for Application No. PCT/US10/38634, dated Aug. 12, 2010.
(Continued)

*Primary Examiner* — David Porta
*Assistant Examiner* — Edwin Gunberg
(74) *Attorney, Agent, or Firm* — Dority & Manning, P.A.

(57) ABSTRACT

A tire surface anomaly detection system and method are disclosed. The system and method are generally based on the principle that a tire surface anomaly will have a different heat transfer rate than that of the uniform mass surrounding the tire surface anomaly. Embodiments of the present disclosure apply thermal energy to the surface of a tire and monitor the infrared energy at the surface of the tire to generate one or more infrared images of the surface of the tire. The infrared images are analyzed by an image processing system to determine and locate thermal gradients on the surface of the tire. The presence of a thermal gradient in the infrared images generally indicates the presence of an anomaly in the surface of the tire. In this manner, the present disclosure provides an objective technique for identifying, locating, and classifying tire surface anomalies.

19 Claims, 8 Drawing Sheets

(56) References Cited

U.S. PATENT DOCUMENTS

| | | | |
|---|---|---|---|
| 4,936,054 A | 6/1990 | Rogers et al. | |
| 5,060,173 A | 10/1991 | Tsuji | |
| 5,060,250 A | 10/1991 | Kwee et al. | |
| 5,396,438 A | 3/1995 | Oblizajek | |
| 5,812,256 A | 9/1998 | Chapin et al. | |
| 6,000,844 A * | 12/1999 | Cramer et al. | 374/5 |
| 6,005,388 A | 12/1999 | Kaefer-Hoffmann et al. | |
| 6,065,331 A | 5/2000 | Fukasawa | |
| 6,304,090 B1 | 10/2001 | Weiss | |
| 6,347,547 B1 | 2/2002 | Moriguchi et al. | |
| 6,600,326 B2 | 7/2003 | Weiss | |
| 6,615,144 B2 | 9/2003 | Williams et al. | |
| 6,840,097 B1 * | 1/2005 | Huber et al. | 73/146 |
| 6,856,929 B1 | 2/2005 | Mawby et al. | |
| 7,082,816 B2 | 8/2006 | Zhu | |
| 7,185,534 B2 | 3/2007 | Stoila et al. | |
| 7,416,624 B2 | 8/2008 | Stoila et al. | |
| 2002/0177959 A1 | 11/2002 | Williams et al. | |
| 2004/0016293 A1* | 1/2004 | Weiss | 73/146 |
| 2006/0123898 A9 | 6/2006 | Zhu | |
| 2006/0262971 A1 | 11/2006 | Foes et al. | |
| 2007/0018803 A1 | 1/2007 | Lang | |
| 2007/0154063 A1 | 7/2007 | Breed | |
| 2008/0011074 A1 | 1/2008 | Braghiroli | |
| 2008/0216567 A1 | 9/2008 | Breed | |
| 2011/0188052 A1* | 8/2011 | Sotgiu | 356/602 |
| 2011/0249115 A1* | 10/2011 | Genest et al. | 348/125 |

FOREIGN PATENT DOCUMENTS

| | | |
|---|---|---|
| EP | 0681181 | 11/1995 |
| FR | 2433178 | 7/1979 |
| JP | 52-78283 | 7/1977 |
| JP | 07-253448 | 10/1995 |
| JP | 11-054735 | 2/1999 |
| JP | 2001141615 | 5/2001 |
| JP | 2005-207763 | 8/2005 |
| JP | 2008-309643 A | 12/2008 |
| JP | 2008-309644 A | 12/2008 |
| JP | 2008-309646 A | 12/2008 |
| WO | WO 2007/076149 | 7/2007 |
| WO | WO 2010/071657 | 6/2010 |

OTHER PUBLICATIONS

Algerlab, Introduction to Vectors Manual [online]; 2003-2011; www.algebralab.org.

International Search Report for Application No. PCT/US10/40561, dated Aug, 31 2010.

International Search Report for Application No. PCT/US2010/038493, dated Aug. 10, 2010.

International Search Report for Application No. PCT/US2011/030467, dated Jun. 13, 2011.

Lucko, et al., "Statistical Considerations for Predicting Residual Value Equipment", *Journal of Construction Engineering and Management*, 132(7), 2006.

\* cited by examiner

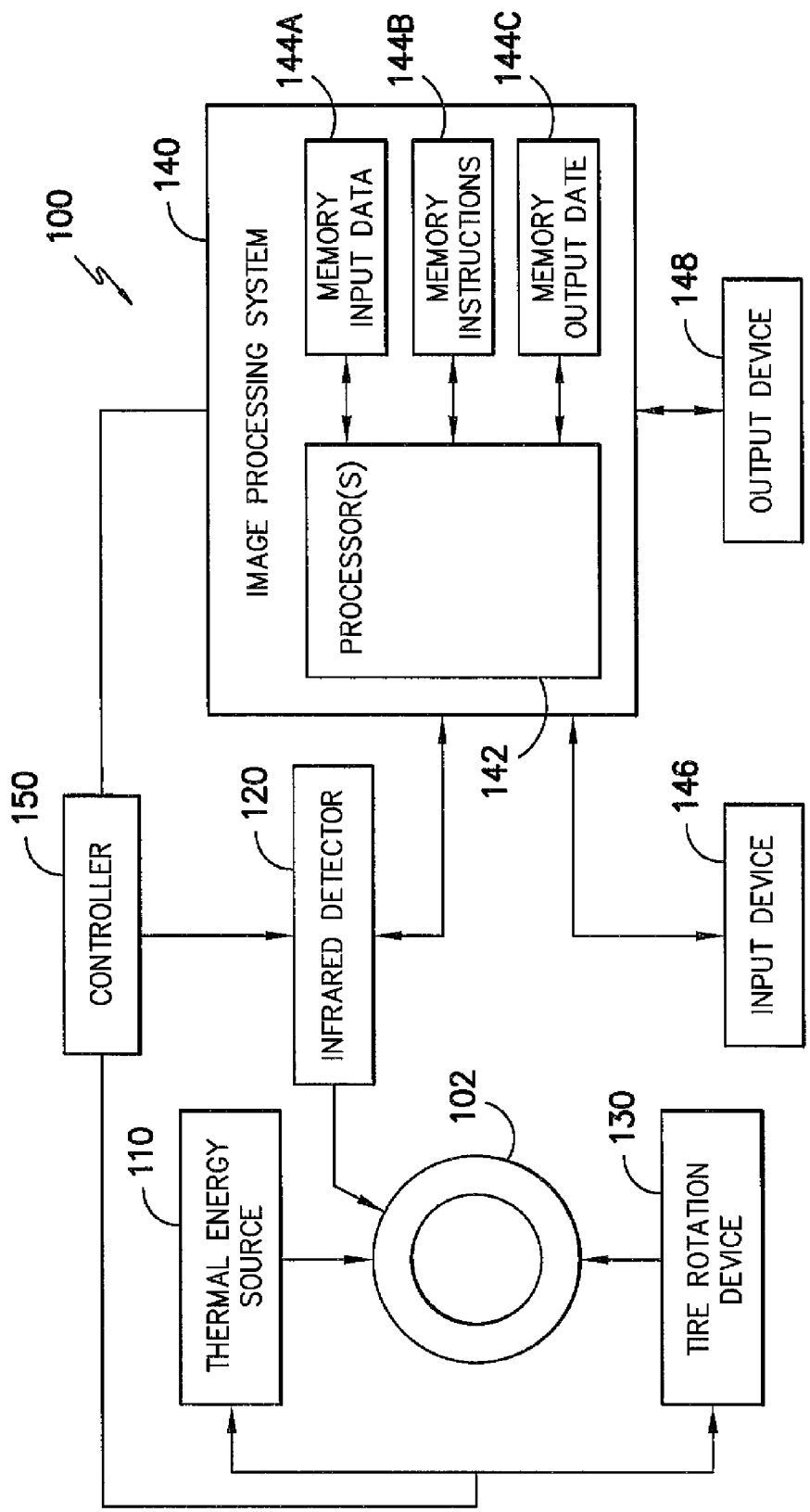
FIG. -1-

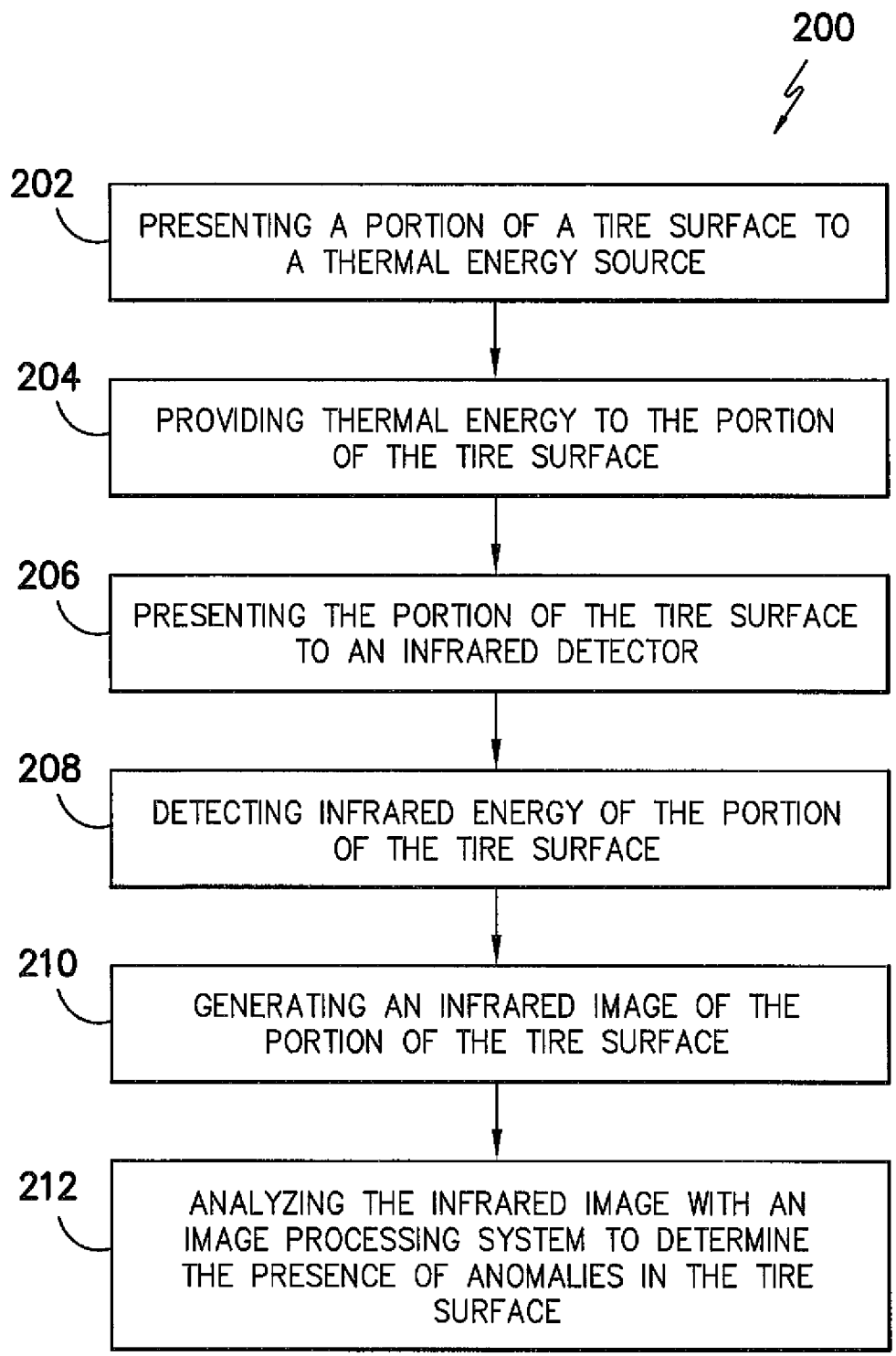
FIG. -2-

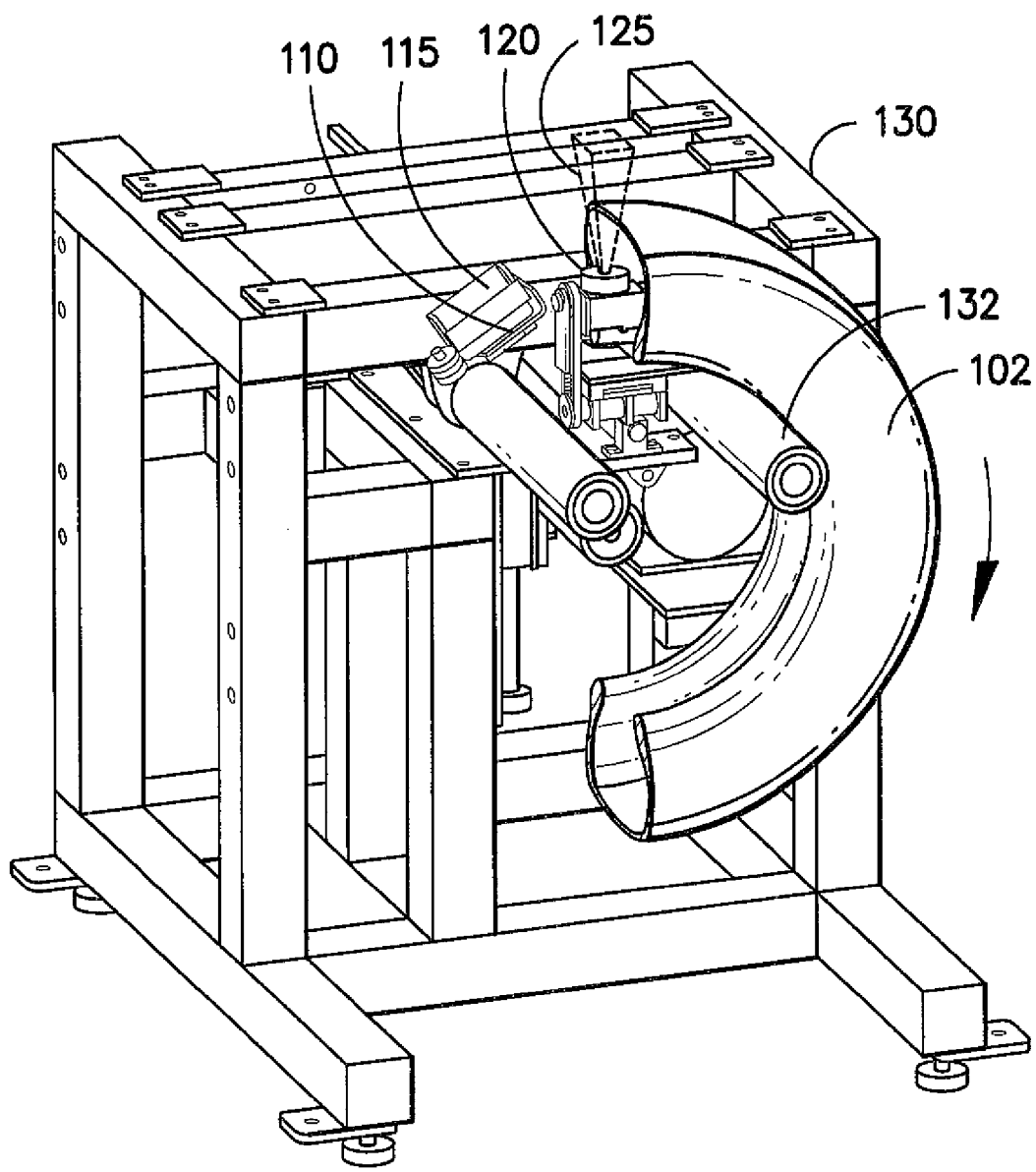
FIG. -3-

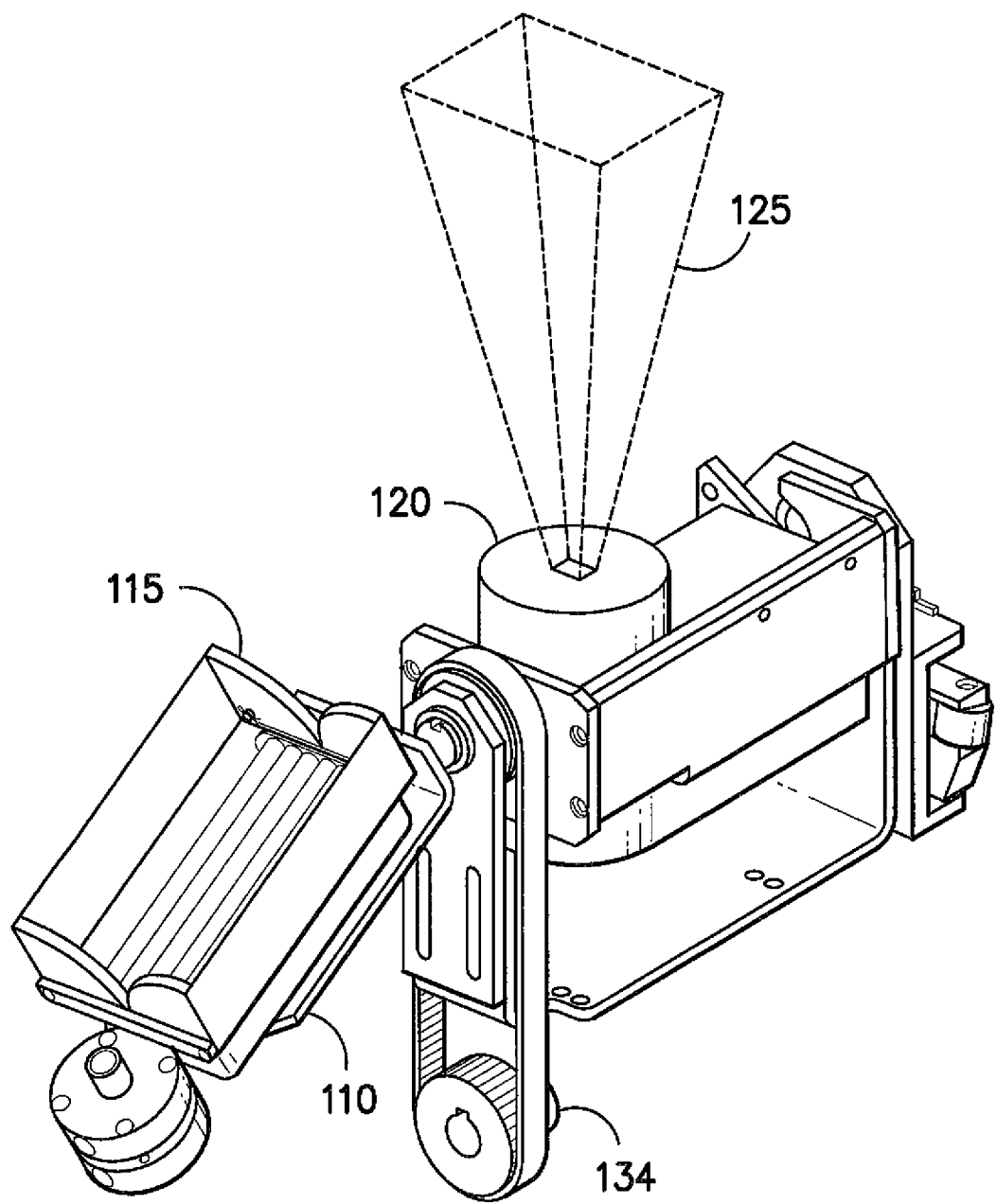
FIG. -4-

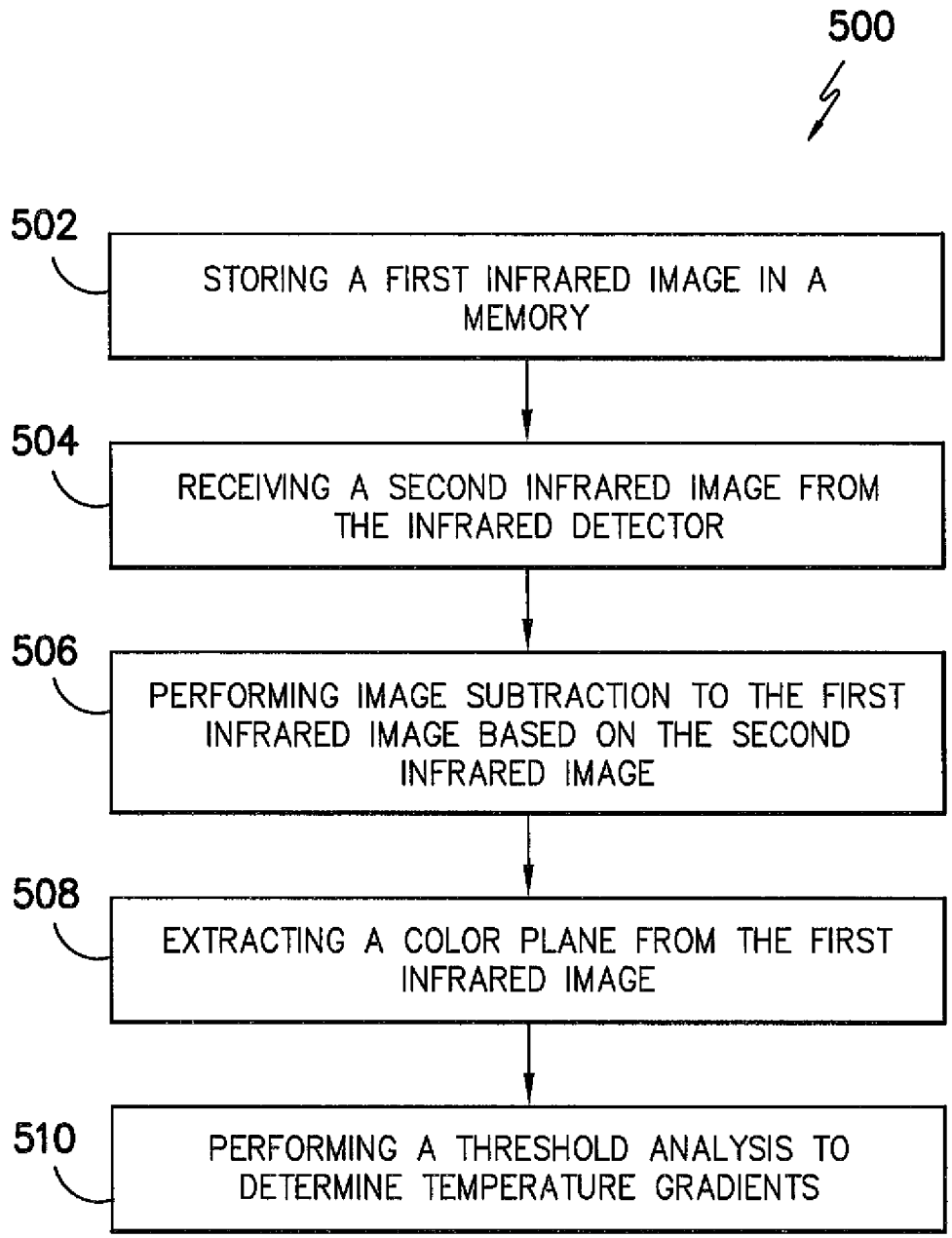
FIG. -5-

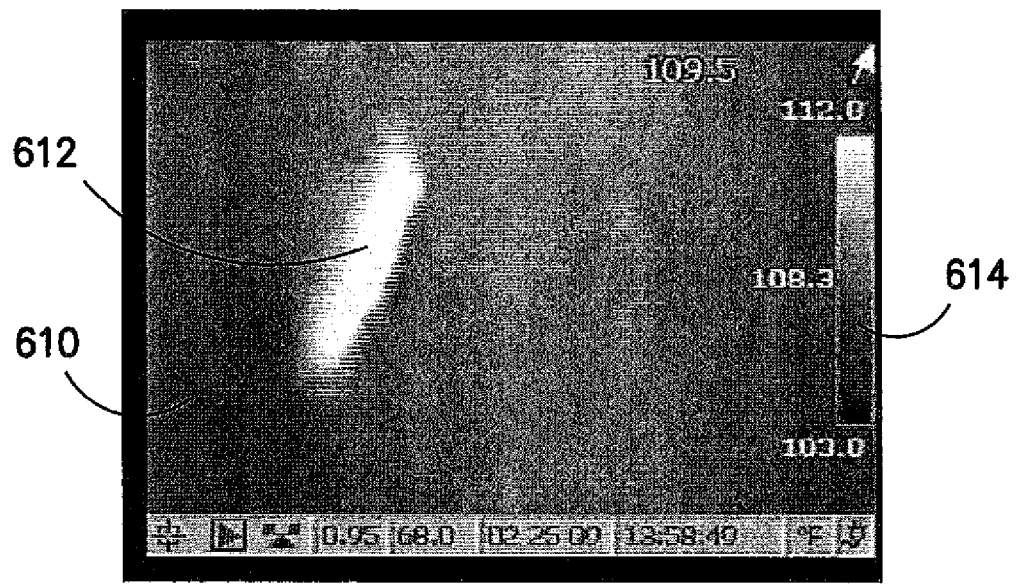
FIG. -6-
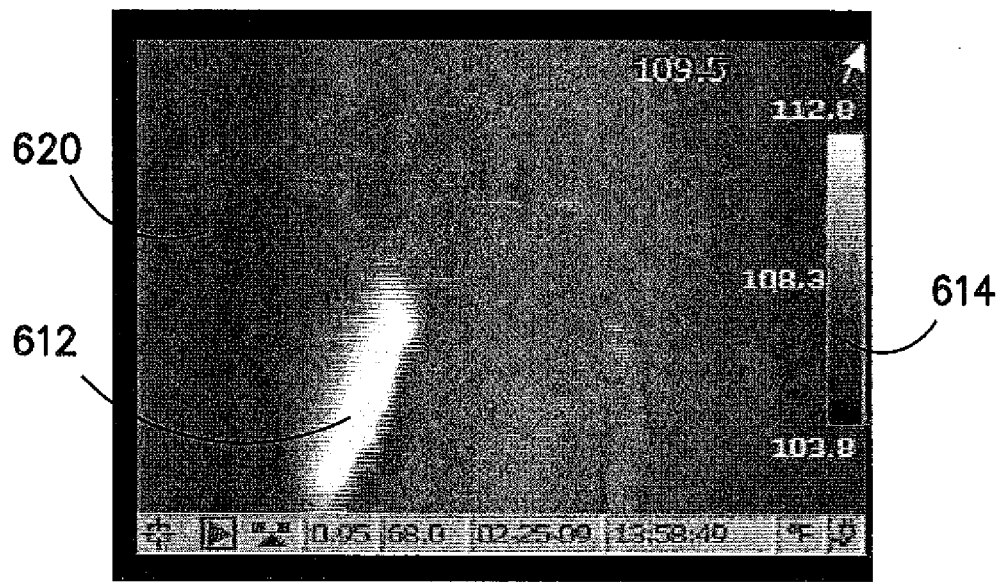
FIG. -7-

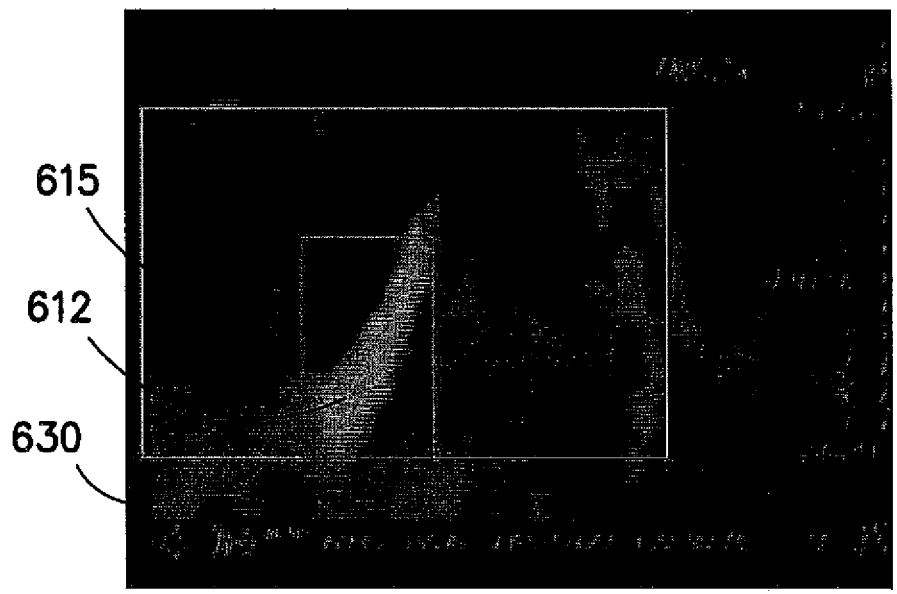
FIG. -8-
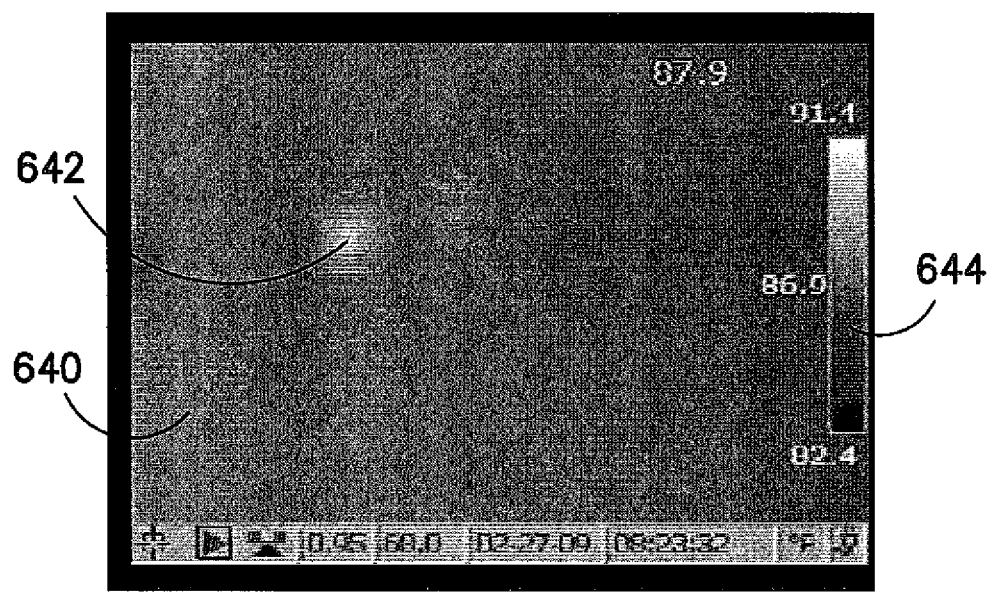
FIG. -9-

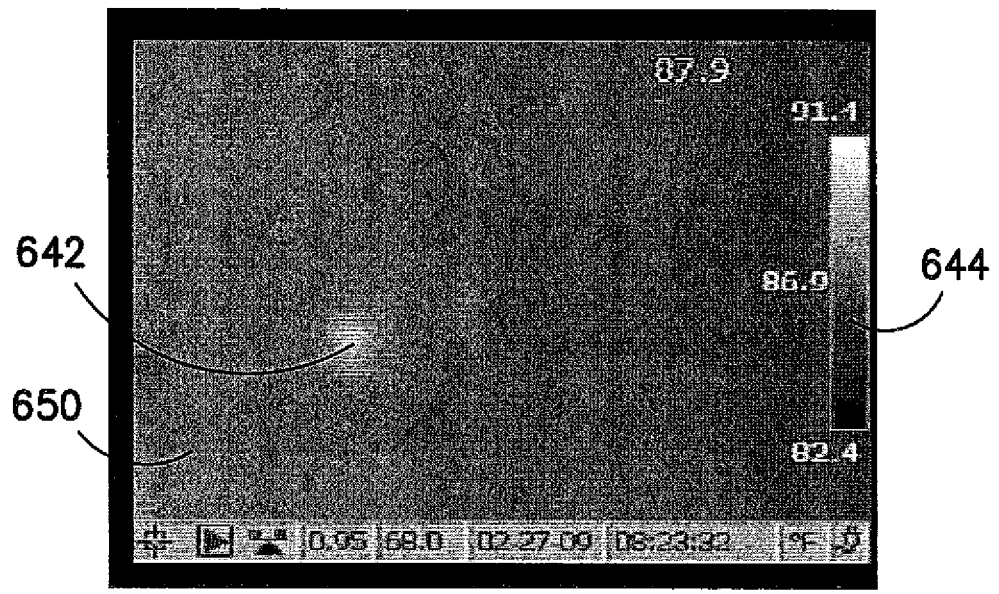
FIG. -10-
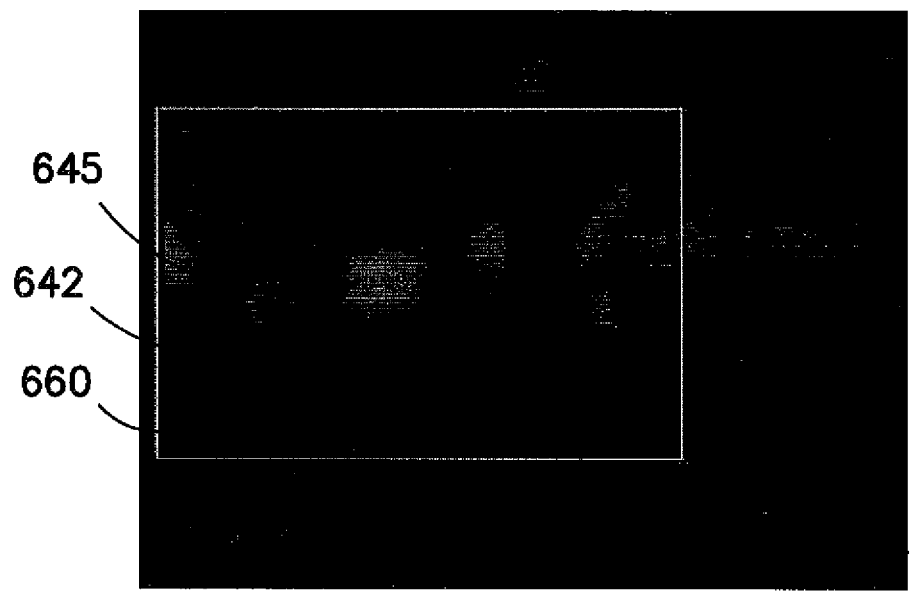
FIG. -11-

TIRE SURFACE ANOMALY DETECTION

FIELD OF THE INVENTION

The present disclosure relates generally to tire testing, and more particularly, to systems and methods for tire surface anomaly detection.

BACKGROUND OF THE INVENTION

Tire repair operations, such as tire retreading operations, are generally used to extend the useful service life of a tire. Typical tire retreading operations include removing previously worn tread from a tire and bonding new tread in its place. Tires may be retread or repaired one or more times as a less expensive alternative to purchasing new tires, providing particular advantages for large-scale operations such as trucking, bussing and commercial aviation.

Generally, some level of non-destructive testing (NDT) of the tire prior to repair is conducted to determine whether it is appropriate to perform the repair operation. Visual inspection methods can be used to validate the integrity and, subsequently, the viability of retread and/or repair of tire casings for retread. For instance, the inside and outside surface of a tire can be visually inspected by an operator using special lighting to inspect for defects such as crazing, cracks, snags, bulges, depressions, gouges, abrasions, marbling, bubbles, blisters, separations, and other defects. Visual inspection methods, however, are subjective, inconsistent, and can require extensive training. Moreover, due to high operator turnover, difficulty exists in retaining expertise.

High Voltage Discharge (HVD) testing can be performed in place of or supplemental to visual inspection. HVD testing can be used to identify anomalies in the inner liner of a tire that penetrate the insulating material of the inner liner. HVD testing, however, will not identify surface anomalies that are not deep enough to sufficiently reduce the dielectric level of the tire so that an electric discharge can occur.

Other NDT techniques include monitoring temperature distribution on the surface of a tire to inspect the tire for delamination. Such techniques, however, can require the application of significant heating or cooling to the surface of the tire, which is not suitable for detecting minor surface anomalies such as pin-holes, abrasions, cracks, or other minor defects on the surface of the tire. Moreover, such techniques can require subjective visual inspection of thermal images of the tire and do not provide for objective identification, location, and classification of surface anomalies.

Thus, a solution is needed for detecting tire surface anomalies during an automated inspection of a tire. The solution can replace the necessity of subjective visual inspection of the tire by providing an objective analysis of surface anomalies that can supplement or replace HVD testing. A solution that can detect minor surface anomalies, such as pin-holes, small cracks, abrasions, and other defects in a tire surface would be particularly useful.

SUMMARY OF THE INVENTION

Aspects and advantages of the invention will be set forth in part in the following description, or may be obvious from the description, or may be learned through practice of the invention.

One exemplary embodiment of the present disclosure is directed to a tire inspection method. The method includes imparting motion to a tire to present a first portion of a tire surface to a thermal energy source; providing thermal energy from the thermal energy source to the first portion of the tire surface; imparting motion to the tire to present the first portion of the tire surface to an infrared detector; detecting infrared energy with the infrared detector from the first portion of the tire surface; generating a first infrared image of the first portion of the tire surface based at least in part on the infrared energy detected from the first portion of the tire surface; and analyzing the first infrared image with an image processing system to determine the presence of one or more anomalies in the tire surface.

In a variation of this exemplary embodiment, providing thermal energy from the thermal energy source can include heating or cooling the first portion of the tire surface. In another variation of this exemplary embodiment, imparting motion to the tire includes continuously rotating an inner surface of the tire over the thermal energy source and the infrared detector. In yet another variation of this exemplary embodiment, the method includes adjusting the location of the thermal energy source relative to the infrared detector to reduce washout effects in the first infrared image.

In still another variation of this exemplary embodiment, the infrared detector detects infrared energy from a scan window at the tire surface. In a particular embodiment, the size of the scan window can be about 25 mm×25 mm at the tire surface. The method can include rotating the infrared detector so that the scan window moves laterally across the inner surface of the tire.

In a further variation of this exemplary embodiment, the first infrared image comprises a plurality of pixels. Each of the pixels can have a pixel value associated with a temperature of the tire surface. In a variation of this exemplary embodiment, analyzing the first infrared image with an image processing system can include performing a pixel thresholding analysis to determine the presence of one or more high or low pixel value regions in the first infrared image.

In still a further variation of this exemplary embodiment, the method can include storing the first infrared image into a memory; imparting motion to the tire to present a second portion of the tire surface to the thermal energy source; providing thermal energy from the thermal energy source to the second portion of the tire surface; imparting motion to the tire to present the second portion of the tire surface to the infrared detector; detecting infrared energy with the infrared detector from the second portion of the tire surface; and generating a second infrared image of the second portion of the tire surface based at least in part on infrared energy detected from the second portion of the surface of the tire. The method can further include performing image subtraction to the first infrared image based on the second infrared image and performing a thresholding analysis on the first infrared image to determine the presence of one or more high or low pixel value regions in the first infrared image.

Another exemplary embodiment of the present disclosure is directed to a tire inspection system. The tire inspection system includes a thermal energy source positioned to provide thermal energy to a first portion of a tire surface and an infrared detector positioned proximate to the thermal energy source. The infrared detector is configured to detect infrared energy from the first portion of the tire surface and to generate a first infrared image based at least in part on the infrared energy detected from the first portion of the tire surface. The system further includes a tire rotation device configured to provide relative motion between the tire and the infrared detector, and an image processing system coupled to the infrared detector. The image processing system is configured to analyze the first infrared image to determine the presence of one or more anomalies in the tire surface.

In a variation of this exemplary embodiment, the thermal energy source comprises a quartz heater. The output of the quartz heater can be about 600 W.

In another variation of this exemplary embodiment, the inner surface of the tire can be placed over the thermal energy source and the infrared detector when the tire is received onto the tire rotation device.

In yet another variation of this exemplary embodiment, the infrared detector can include an infrared camera or an array of infrared sensitive photoelectric diodes.

In still another variation of this exemplary embodiment, the infrared detector is configured to detect infrared energy from a scan window at the tire surface. The scan window can have a size of approximately 25 mm×25 mm at the tire surface.

In a further variation of this exemplary embodiment, the image processing system is configured to perform a thresholding analysis on the first infrared image to determine the presence of one or more high or low pixel value regions in the first infrared image.

In yet a further variation of this exemplary embodiment, the infrared detector is configured to detect infrared energy from a second portion on the tire surface and to generate a second image based at least in part on the infrared energy detected from the second portion of the tire surface. The image processing system can be further configured to perform image subtraction on the first infrared image based at least in part on the second infrared image.

Variations and modifications can be made to these exemplary embodiments of the present disclosure.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWING

A full and enabling disclosure of the present invention, including the best mode thereof, directed to one of ordinary skill in the art, is set forth in the specification, which makes reference to the appended figures, in which:

FIG. 1 illustrates a block diagram of an exemplary system according to an exemplary embodiment of the present disclosure;

FIG. 2 illustrates a flow chart of exemplary method steps according to an exemplary embodiment of the present disclosure;

FIG. 3 illustrates a perspective view of an exemplary thermal energy source and exemplary infrared detector according to an exemplary embodiment of the present disclosure;

FIG. 4 illustrates a close up perspective view of an exemplary thermal energy source and exemplary infrared detector according to an exemplary embodiment of the present disclosure;

FIG. 5 depicts a flow diagram of an exemplary image analysis method according to an exemplary embodiment of the present disclosure;

FIG. 6 depicts an exemplary first infrared image that can be analyzed in accordance with exemplary embodiments of the present disclosure;

FIG. 7 depicts an exemplary second infrared image that can be analyzed in accordance with exemplary embodiments of the present disclosure;

FIG. 8 depicts the exemplary infrared image of FIG. 7 after being subjected to image subtraction techniques;

FIG. 9 depicts an exemplary first infrared image that can be analyzed in accordance with exemplary embodiments of the present disclosure;

FIG. 10 depicts an exemplary second infrared image that can be analyzed in accordance with exemplary embodiments of the present disclosure; and FIG. 11 depicts the exemplary infrared image of FIG. 9 after being subjected to image subtraction techniques.

DETAILED DESCRIPTION OF THE INVENTION

For purposes of describing the invention, reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention covers such modifications and variations as come within the scope of the appended claims and their equivalents.

Generally, the present disclosure is directed to tire surface anomaly detection. A tire surface anomaly will have a different heat transfer rate than that of the uniform mass surrounding the tire surface anomaly. Based on this principle, embodiments of the present disclosure apply thermal energy, such as forced air heat or forced air cooling, to the surface of a tire and monitor the infrared energy at the surface of the tire to generate one or more infrared images of the surface of the tire. The infrared images can be analyzed by an image processing system to determine and locate thermal gradients on the surface of the tire. The presence of a thermal gradient in the infrared images generally indicates the presence of an anomaly in the surface of the tire. In this manner, the present disclosure provides an objective technique for identifying, locating, and classifying tire surface anomalies.

FIG. 1 illustrates a schematic overview of an exemplary tire testing system 100 according to an exemplary embodiment of the present disclosure. Tire testing system 100 can be used to perform NDT techniques to a tire 102 to determine if a surface of tire 102 has surface anomalies and to determine whether tire 102 is viable for repair or retread. As used herein, the term "surface anomaly" can refer to any irregularity in a surface of a tire, including defects in the tire such as crazing, cracks, snags, bulges, depressions, gouges, abrasions, marbling, bubbles, blisters, separations, and other defects.

Tire testing system 100 includes a thermal energy source 110, an infrared detector 120, a tire rotation device 130, and an image processing system 140. Thermal energy source 110 is used provide thermal energy, such as heating or cooling, to a surface of tire 102. For instance, in a particular embodiment, thermal energy source 110 is configured to provide a hot air blast or cool air blast to a surface of tire 102. In a particular implementation, the thermal energy source 110 includes a 600 W quartz heater that radiates heat onto a surface of tire 102.

Infrared detector 120 is used to detect infrared energy of a portion of the surface of tire 102 after thermal energy source 110 has provided thermal energy to the tire surface. Infrared detector 120 is configured to generate infrared images of a portion of the tire surface based on the detected infrared energy. Infrared detector 120 can be an infrared camera, an array of infrared sensitive photodiodes, or any other suitable device capable of detecting infrared energy from a surface of a tire. Because the heat transfer characteristics of surface anomalies are less than the heat transfer characteristics of the surrounding mass, the infrared images will generally depict temperature gradients in the surface of the tire that are representative of tire surface anomalies. As will be discussed in more detail below, image processing system 140 is used to analyze infrared images generated by infrared detector 120 to determine the presence of one or more anomalies in the surface of the tire.

Referring to FIG. 2, a flow chart describing the exemplary steps of a method 200 that can be performed using thermal energy source 110, infrared detector 120, and image processing system 140 will be set forth. At 202, the method 200 includes presenting a portion of a tire surface to thermal energy source 110. For instance, in a particular embodiment, a tire rotation device 130 (shown in FIG. 1) can be used to impart motion to tire 102 to present a portion of the surface of tire 102 to thermal energy source 110.

At 204, thermal energy is provided to the portion of the tire surface from the thermal energy source 110. For instance, thermal energy source 110 can provide a blast of cool or hot air to the portion of the tire surface. Those of ordinary skill in the art, using the disclosures provided herein, should understand that any method of cooling or heating the tire surface can be used without deviating from the scope of the present invention.

As the tire surface is presented to the thermal energy source 110, thermal energy is induced into the tire at varying rates depending on the heat transfer rate of the localized surface. For instance, an anomaly at the surface of the tire will have a different heat transfer rate than the surrounding tire mass. Temperature gradients will be formed at the tire surface proximate to the location of the anomaly. The temperature gradients can be used to detect the presence of anomalies in the surface of the tire.

At 206, the portion of the tire surface previously exposed to thermal energy from the thermal energy source 110 is presented to an infrared detector 120. For example, tire rotation device 130 can be used to impart further motion to tire 102 to present the tire surface to infrared detector 120. At 208, infrared detector 120 detects infrared energy from the portion of the tire surface previously irradiated with thermal energy and generates an infrared image based on the detected infrared energy as illustrated at 210. Thermal gradients caused by anomalies in the tire surface will be visible on the infrared image generated by infrared detector 120. At 212, the image processing system 140 analyzes the infrared image to objectively determine the existence of any thermal gradients in the infrared image, and thus, the presence of anomalies in the tire surface.

Referring to FIG. 3 and FIG. 4, an exemplary arrangement of tire 102, thermal energy source 110, infrared detector 120, and tire rotation device 130 will be discussed in detail. As illustrated in FIG. 3, thermal energy source 110 and infrared detector 120 are mounted to tire rotation device 130. Tire rotation device 130 includes one or more rollers 132. Tire 102 is placed over the top of thermal energy source 110 and infrared detector 120 so that thermal energy source 110 and infrared detector 120 can inspect and test the inner liner or inner surface of tire 102. The tire bead of tire 102 rests on one or more rollers 132. The rollers 132 are configured to impart motion to tire 102, for instance by continuously rotating tire over thermal energy source 110 and infrared detector 120. In a particular embodiment, tire 102 can be rotated in the clockwise direction over thermal energy source 110 and infrared detector 120 at a rate of 50 seconds per revolution.

In operation, tire rotation device 130 rotates the tire 102 so that a portion of the inner surface of tire 102 is first presented to thermal energy source 110. Thermal energy source 110 can be positioned so that the face of thermal energy source 110 is normal to the inner surface of the tire 102. The thermal energy source 110 is preferably positioned a sufficient distance from the inner surface of the tire to prevent "washout effects" in the infrared images generated by infrared detector 120. Washout effects can occur, for instance, if a portion of the tire surface is irradiated with so much thermal energy that the temperature of the tire surface falls outside or at the high end of the grayscale or color range of the infrared images generated by infrared detector 120.

FIG. 4 depicts a close-up perspective view of thermal energy source 110. As illustrated, thermal energy source 110 can include shutters 115 that can be held closed during the initial power up state of thermal energy source 110. The shutters 115 can be opened when the thermal energy source has reached a consistent thermal output to allow for consistent transfer of thermal energy during tire testing. This provides for more uniform and objective analysis of tire surface anomalies.

Referring back to FIG. 3, tire rotation device 130 can be configured to continuously rotate the inner surface of tire 102 over both the thermal energy source 110 and the infrared detector 120 so that a portion of the tire surface is presented to the infrared detector 120 subsequent to being irradiated with thermal energy by the thermal energy source 110. Infrared detector 120 detects infrared energy from the portion of the tire surface and generates infrared images based on infrared energy detected from the portion of the tire surface. Exemplary infrared images generated by infrared detector are illustrated in FIGS. 6, 7, 9, and 10.

Infrared detector 120 can be any device or apparatus capable of generating an infrared image based on infrared energy of the tire surface presented to infrared detector 120, such as an infrared camera, an array of infrared sensitive photodiodes, or other suitable infrared detector. In one exemplary embodiment, the infrared detector 120 includes an infrared camera capable of generating a gray scale image based on the infrared energy detected by the infrared image. The pixel value of a pixel in the grayscale image can be associated with the infrared energy and the temperature of the portion of the tire surface analyzed by the infrared detector. The grayscale to temperature relationship can be manually set on the infrared camera, or automatically adjusted by the infrared camera. In other embodiments, the infrared camera can be configured to generate a two dimensional data array that includes pixel values associated with an exact temperature measurement of the surface of the tire. The temperature measurement is based on the infrared energy of the tire surface.

As illustrated in FIG. 3 and FIG. 4, the infrared detector 120 analyzes infrared energy from a portion tire surface that falls within a scan window 125 of the infrared detector 120. As tire 102 rotates, scan window 125 passes over the inner surface of the tire 102 and detects infrared energy from different portions of tire 102 along the circumference of the inner surface of tire 102. Infrared detector 120 detects infrared energy from the portion of the tire surface presented to the scan window 125. Depending on the image output rate of the infrared detector 120, infrared images are generated from the infrared energy detected in the scan window 125. For instance, in a particular embodiment, infrared images are generated at a rate of 30 images per second. These infrared images can be processed by image processing system 140 to objectively identify and locate tire surface anomalies.

In certain embodiments, the size of scan window 125 is smaller than the size of the inner surface of tire 102. To address this concern, infrared detector 120 can be connected to a rotating mechanism 134 that rotates the infrared detector 120 in the tire rotating device 130 so that the scan window 125 moves laterally across the inner surface of tire 102. In this manner, the infrared detector 120 and scan window 125 are capable of rotating from bead to bead of tire 102 to allow presentation of the entire inside surface of tire 102 to the infrared detector 120.

For instance, in a particular implementation, tire rotation device 130 imparts motion to tire 102 so that tire 102 continuously rotates over thermal energy source 110 and infrared detector 120. Infrared detector 120 continuously generates infrared images of the tire surface as the tire 102 rotates around the thermal energy source 110 and infrared detector 120. After the tire 102 has completed one revolution, the rotating mechanism 134 can move infrared detector 120 an incremental step in the lateral direction across the inner surface of tire 102. The tire rotation device 130 then continuously rotates the tire 102 so that infrared detector 120 scans a different portion of the tire surface.

In one exemplary embodiment, scan window 125 of infrared detector 120 is relatively small, such as about 25 mm×25 mm, so that minor defects such as pin-holes in the inner surface of the tire can be detected. In this particular embodiment, the amount of and rate of thermal energy applied to the tire surface should be controlled to avoid washout effects in infrared images associated with the relatively small scan window 125. Radiating a large amount of thermal energy onto the tire surface may washout thermal gradients in the relatively small scan window 125, reducing the ability of the tire testing techniques of the present disclosure to objectively and accurately identify and locate minor surface anomalies.

In a particular embodiment, the thermal energy source can be a quartz heater having a thermal output of about 600 W. This amount of heat energy allows for sufficient thermal gradients to be generated in the relatively small scan window 125 of infrared detector 120 so that minor anomalies, such as pin-holes, small abrasions, and small cracks can be detected in the surface of tire 102. To further reduce washout effects, the thermal energy source 110 can be positioned a sufficient distance from the infrared detector 120 so that there is enough time for temperature gradients to form in the surface of tire 102 after being exposed to the thermal energy source 110. For instance, in particular embodiments, the location where the portion of the tire surface is presented to the thermal energy source 110 and the location where the portion of the tire surface is presented to the infrared detector 120 can be separated by an angular distance based on the center of tire 102 of about 5° to about 30°, such as about 10° to about 20°, such as about 15°, or 20°, or any other angular distance or range of angular distances between about 5° and about 30°.

Referring back to FIG. 1, details concerning the image processing system 140 will now be set forth. The infrared images obtained by infrared detector 120 can be relayed to the image processing system 140, which can include one or more processors 142. Processor(s) 142 can be configured to receive input data including infrared images from infrared detector 120, analyze such infrared images with suitable image analysis techniques, and provide useable output such as data to a user or signals to a process controller 150.

Various memory/media elements 144 may be provided as a single or multiple portions of one or more varieties of computer-readable media, such as, but not limited to, any combination of volatile memory (e.g., random access memory (RAM, such as DRAM, SRAM, etc.) and nonvolatile memory (e.g., ROM, flash, hard drives, magnetic tapes, CD-ROM, DVD-ROM, etc.) or any other memory devices including diskettes, drives, other magnetic-based storage media, optical storage media and others. Although FIG. 1 shows three separate memory/media elements 144a, 144b and 144e, the content dedicated to such devices may actually be stored in one memory/media element or in multiple elements. Any such possible variations and other variations of data storage, using the disclosures provided herein, will be appreciated by one of ordinary skill in the art.

The computing/processing devices of FIG. 1 may be adapted to function as a special-purpose machine providing desired functionality by accessing software instructions rendered in a computer-readable form stored in one or more of the memory/media elements (e.g., memory/media element 144b). When software is used, any suitable programming, scripting, or other type of language or combinations of languages may be used to implement the teachings contained herein. In other embodiments, the methods disclosed herein may alternatively be implemented by hard-wired logic or other circuitry, including, but not limited to application-specific circuits.

Other memory/media elements (e.g., memory/media elements 144a, 144e) are used to store data which will also be accessible by the processor(s) 142 and which will be acted on per the software instructions stored in memory/media element 144b. For example, memory/media element 144a can include input data corresponding to infrared images obtained from the infrared detector 120 as well as any predetermined parameters, such as but not limited to pixel to temperature relationship, image pixel range, control parameters, such as infrared camera parameters, thermal energy source parameters, tire rotation parameters, other suitable control parameters, and tire parameters, such as tire radius, tire width, tire summit mass, tire pressure, tire radial stiffness, tire tangential stiffness, tire bending stiffness, tire extensional stiffness, tread locations, general tire data and the like. Such predetermined parameters may be pre-programmed into memory/media element 144a or provided for storage therein when entered as input data from a user accessing the input device 146.

Input device 146 may correspond to one or more peripheral devices configured to operate as a user interface with image processing system 140. Exemplary input devices may include but are not limited to a keyboard, touch-screen monitor, microphone, mouse and other suitable input devices.

Second memory element 144b includes computer-executable software instructions that can be read and executed by processor(s) 142 to act on the input data stored in memory/media element 144a to create new output data (e.g., surface anomaly identification, location, and classification) for storage in a third memory/media element 144c. Selected portions of the output data may then be provided to one or more peripheral output devices 148.

Output device 148 may correspond to a display such as a monitor, screen, or other visual display, a printer, or the like. Another specific form of output device may correspond to a process controller 150. In one embodiment, process controller 150 assists the overall tire manufacturing process by coordinating operating parameters of thermal energy source 110, infrared detector 120 and tire rotation device 130.

Referring to FIG. 5 an exemplary method 500 of image processing steps for objectively analyzing infrared images to identify and locate surface anomalies will now be discussed. At 502, a first infrared image is stored in a memory, such as memory 144a, of image processing system 140.

An exemplary first infrared image 610 is depicted in FIG. 6. First infrared image 610 is an infrared image of an about a 25 mm×25 mm portion of a tire surface. As illustrated, exemplary infrared image 610 includes a high pixel value region 612 where the pixel value of the infrared image 610 is higher than the remainder of the infrared image 610. The grayscale scale 614 is depicted in the right side of infrared image 610. High pixel value region 612 generally indicates the presence of a temperature gradient in the surface of the tire. This temperature gradient could be associated with a minor surface anomaly, such as a minor cut in the tire surface.

While visual inspection of infrared image 610 may indicate the presence of high pixel value region 612 in infrared image 610, such visual inspection remains subjective and does not provide an objective technique for determining the presence of surface anomalies. For instance, a visual inspection of infrared image 640 of FIG. 9 may overlook high pixel region 642. Moreover, due to the high volume of infrared images generated in scanning the entire surface of a tire, visual inspection of each individual infrared image may not practical or economically feasible.

To provide an automated and objective approach to analyzing the infrared images generated by infrared detector 120, image processing system 140 can perform image processing techniques to identify and locate surface anomalies in the tire surface. For instance, as illustrated at block 510 of method 500, image processing system 140 can perform a thresholding analysis on an infrared image, such as bright cluster analysis techniques or dark cluster analysis techniques. The thresholding analysis generally scans the pixel values of an infrared image and determines a region of the infrared image where the pixel values are greater than or less than the pixels of the surrounding image. Such thresholding analysis provides an objective technique for locating anomalies on the tire surface. The thresholding analysis of infrared images can be performed with or without performing intermediate image processing steps to the infrared images.

Due to operating parameters of infrared detector 120, however, various image processing steps may be performed to increase the accuracy of anomaly detection by image processing system 140. For example, as a surface of a tire is continuously presented to thermal energy source 110, the ambient temperature of the tire surface can rise throughout the duration of the test. If the grayscale or pixel value to temperature range of the infrared detector 120 is not properly adjusted during the test, the infrared images generated by infrared detector 120 may be washed out at the high end of the range, effectively hiding surface anomalies in the infrared image or causing false detection of the ambient background of the infrared image as a surface anomaly.

One approach to avoid these washout effects is to allow the infrared detector 120 to automatically adjust its range. However, this often cannot be performed quickly enough given the transfer rate of thermal energy from the thermal energy source 110 and the speed of motion of the tire surface relative to the infrared detector 120.

Another approach is to use image subtraction techniques during the image processing analysis. For example, referring to FIG. 5 at block 504, the image processing system 140 can receive a second infrared image from infrared detector 120. The second infrared image can be one of many infrared images that are generated by infrared detector 120 as the tire surface is passed over infrared detector 120. Preferably, the second infrared image is the next incremental infrared image generated by infrared detector 120 after generation of the first infrared image.

An exemplary second infrared image 620 is illustrated in FIG. 7. High pixel value portion 612 is still visible in infrared image 620, but is depicted lower in the infrared image 620 due to the motion of the tire surface relative to the infrared detector 120. Referring to FIG. 5 at 506, the image processing system 140 can perform image subtraction to the first infrared image based on the second infrared image. The resulting image 630 is depicted in FIG. 8. As illustrated, the image subtraction process removed the washed out ambient background while leaving the high pixel value region 612 visible. Thresholding techniques can then be more accurately performed to image 630 due to the removal of the ambient background.

Further processing can be performed to image 630 to objectively identify surface anomalies of a tire. For instance, as indicated at block 508 of FIG. 5, a color plane, such as either the red, green, or blue color plane, can be extracted from the infrared image. This process step may or may not be necessary depending on the operating parameters of the infrared detector 120 and image processing system 140. At block 510, thresholding analysis 510 can be performed to objectively locate and identify high pixel regions, and correspondingly, surface anomalies in a tire. As illustrated in FIG. 8, image thresholding analysis was used to identify high pixel value region 612 and to highlight high pixel region 612 with identification rectangle 615. High pixel region 612 can be associated with a minor surface anomaly in a tire, such as a minor abrasion or crack in the surface of a tire.

FIGS. 9 to 11 illustrate the exemplary detection of a minor pin-hole anomaly in a tire surface through analysis of infrared images generated by infrared detector 120. First infrared image 640 illustrates an exemplary first infrared image generated by infrared detector 120 and received or stored at image processing system 140. First infrared image 640 includes a high pixel value region 642. The grayscale scale 644 is depicted on the right side of first infrared image 640.

FIG. 10 depicts an exemplary second infrared image 650 that is stored or received at image processing system 140 after first infrared image 640. High pixel value portion 642 is still visible in infrared image 650, but is depicted lower in the infrared image 650 due to the motion of the tire surface relative to the infrared detector 120. FIG. 11 depicts a resulting image 660 after image subtraction is performed on first infrared image 640 based on second infrared image 650. As illustrated, the image subtraction process removed the ambient background while leaving the high pixel value region 642 visible. Image thresholding techniques were used to identify high pixel value region 642 and to highlight high pixel value region 642 with identification rectangle 645. High pixel value region 642 is representative of a thermal gradient on the surface of a tire and can indicate the presence of a pin-hole surface anomaly.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A tire inspection method, comprising:
   imparting motion to a tire with a tire rotation device to present a first portion of a tire inner surface to a thermal energy source;
   providing thermal energy from the thermal energy source to the first portion of the tire surface;
   imparting motion to the tire with the tire rotation device to present the first portion of the tire inner surface to an infrared detector, the infrared detector being separated from the thermal energy source by an angular distance based on a center of the tire in the range of 5° to 30°;
   detecting infrared energy from the first portion of the tire inner surface with the infrared detector;
   generating a first infrared image of the first portion of the tire inner surface based at least in part on the infrared energy detected from the first portion of the tire inner surface; and
   analyzing the first infrared image with an image processing system using image subtraction to determine the presence of one or more anomalies in the tire inner surface;
   wherein imparting motion to the tire comprises continuously rotating the tire inner surface over the thermal energy source and the infrared detector.

2. The tire inspection method of claim 1, wherein providing thermal energy from the thermal energy source comprises heating or cooling the first portion of the tire inner surface.

3. The tire inspection method of claim 1, wherein the method comprises adjusting the location of the thermal energy source relative to the infrared detector to reduce washout effects in the first infrared image.

4. The tire inspection method of claim 1, wherein the infrared detector detects infrared energy from a scan window at the tire inner surface, the method further comprising rotating the infrared detector so that the scan window moves laterally across the tire inner surface.

5. The tire inspection method of claim 1, wherein the infrared detector is configured to detect infrared energy from a scan window at the tire surface, the scan window having a size of about 25 mm×25 mm at the tire inner surface.

6. The tire inspection method of claim 1, wherein the first infrared image comprises a plurality of pixels, each pixel having a pixel value associated with a temperature of the tire inner surface.

7. The method of claim 6, wherein analyzing the first infrared image with an image processing system comprises performing a pixel thresholding analysis to determine the presence of one or more high or low pixel value regions in the first infrared image.

8. The method of claim 1, wherein the method comprises:
   storing the first infrared image into a memory;
   imparting motion to the tire to present a second portion of the tire inner surface to the thermal energy source;
   providing thermal energy from the thermal energy source to the second portion of the tire inner surface;
   imparting motion to the tire to present the second portion of the tire inner surface to the infrared detector;
   detecting infrared energy with the infrared detector from the second portion of the tire inner surface; and
   generating a second infrared image of the second portion of the tire inner surface based at least in part on infrared energy detected from the second portion of the surface of the tire.

9. The method of claim 8, wherein analyzing the first infrared image with the image processing system comprises:
   performing image subtraction to the first infrared image based on the second infrared image; and
   performing a thresholding analysis on the first infrared image to determine the presence of one or more high or low pixel value regions in the first infrared image.

10. A tire inspection system, comprising:
    a thermal energy source positioned to provide thermal energy to a first portion of a tire inner surface;
    an infrared detector separated from the thermal energy source by an angular distance based on a center of the tire in the range of 5° to 30°, said infrared detector configured to detect infrared energy from the first portion of the tire inner surface and to generate a first infrared image based at least in part on the infrared energy detected from the first portion of the tire inner surface;
    a tire rotation device configured to continuously rotate the tire inner surface over the thermal energy source and the infrared detector; and
    an image processing system coupled to the infrared detector, the image processing system configured to analyze the first infrared image using image subtraction to determine the presence of one or more anomalies in the tire inner surface.

11. The tire inspection system of claim 10, wherein the thermal energy source comprises a quartz heater.

12. The tire inspection system of claim 11, wherein the output of the quartz heater is about 600W.

13. The tire inspection system of claim 10, wherein the tire inner surface is placed over the thermal energy source and the infrared detector when the tire is received onto the tire rotation device.

14. The tire inspection system of claim 10, wherein the infrared detector comprises an infrared camera.

15. The tire inspection system of claim 10, wherein the infrared detector comprises a plurality of photoelectric diodes sensitive to infrared energy.

16. The tire inspection system of claim 10, wherein the infrared detector is configured to detect infrared energy from a scan window at the tire surface, the scan window having a size of approximately 25 mm×25 mm at the tire inner surface.

17. The tire inspection system of claim 10, wherein the image processing system is configured to perform a thresholding analysis on the first infrared image to determine the presence of one or more high pixel regions in the first infrared image.

18. The tire inspection system of claim 10, wherein the infrared detector is configured to detect infrared energy from a second portion on the tire inner surface and to generate a second infrared image based at least in part on the infrared energy detected from the second portion of the tire inner surface.

19. The tire inspection system of claim 18, wherein the image processing system is configured to perform image subtraction on the first infrared image based at least in part on the second infrared image.

* * * * *